United States Patent [19]

Bailey

[11] 4,133,304

[45] Jan. 9, 1979

[54] SYRINGE-LIKE APPARATUS WITH REMOVABLE CAPILLARY CARTRIDGE

[75] Inventor: Donald L. Bailey, Thornton, Colo.

[73] Assignee: EMDE Corporation, Reno, Nev.

[21] Appl. No.: 792,241

[22] Filed: Apr. 29, 1977

[51] Int. Cl.² .............................................. A61B 5/00
[52] U.S. Cl. ............................... 128/2 F; 128/DIG. 5
[58] Field of Search ................. 128/2 F, DIG. 5, 215, 128/218 R, 218 P, 218 G, 234, 272.3

[56] References Cited

U.S. PATENT DOCUMENTS

| 3,159,159 | 12/1964 | Cohen ................................... 128/2 F |
| 3,216,616 | 11/1965 | Blankenship, Jr. ........... 128/218 R X |
| 3,395,696 | 8/1968 | Brown et al. .......................... 128/2 F |

*Primary Examiner*—John D. Yasko
*Attorney, Agent, or Firm*—Crandell and Polumbus

[57] ABSTRACT

A hollow capillary tube or cartridge is received within the interior of a hollow tubular syringe-like device to collect a blood sample. A fluid inlet means of the capillary cartridge connects in a fluid conductive relationship with a hypodermic needle attached to the syringe-like device to conduct a blood sample to the interior of the capillary cartridge. A fluid outlet means of the capillary cartridge allows the blood sample to fill the capillary cartridge by expelling air from the interior of capillary cartridge. The fluid outlet means includes a removable piece of fluid conductive fibrous material which allows the air to escape as the blood sample is received and which conducts a small amount of blood sample when the capillary cartridge is completely filled. Means for creating a pressure less than ambient pressure at the fluid outlet means of the capillary cartridge may be employed when the arterial blood pressure of the individual from whom the blood sample is collected is less than sufficient to naturally fill the interior of the capillary cartridge. Crystalline heparin deposited on the interior of the capillary tube prevents clotting of the collected blood sample.

39 Claims, 12 Drawing Figures

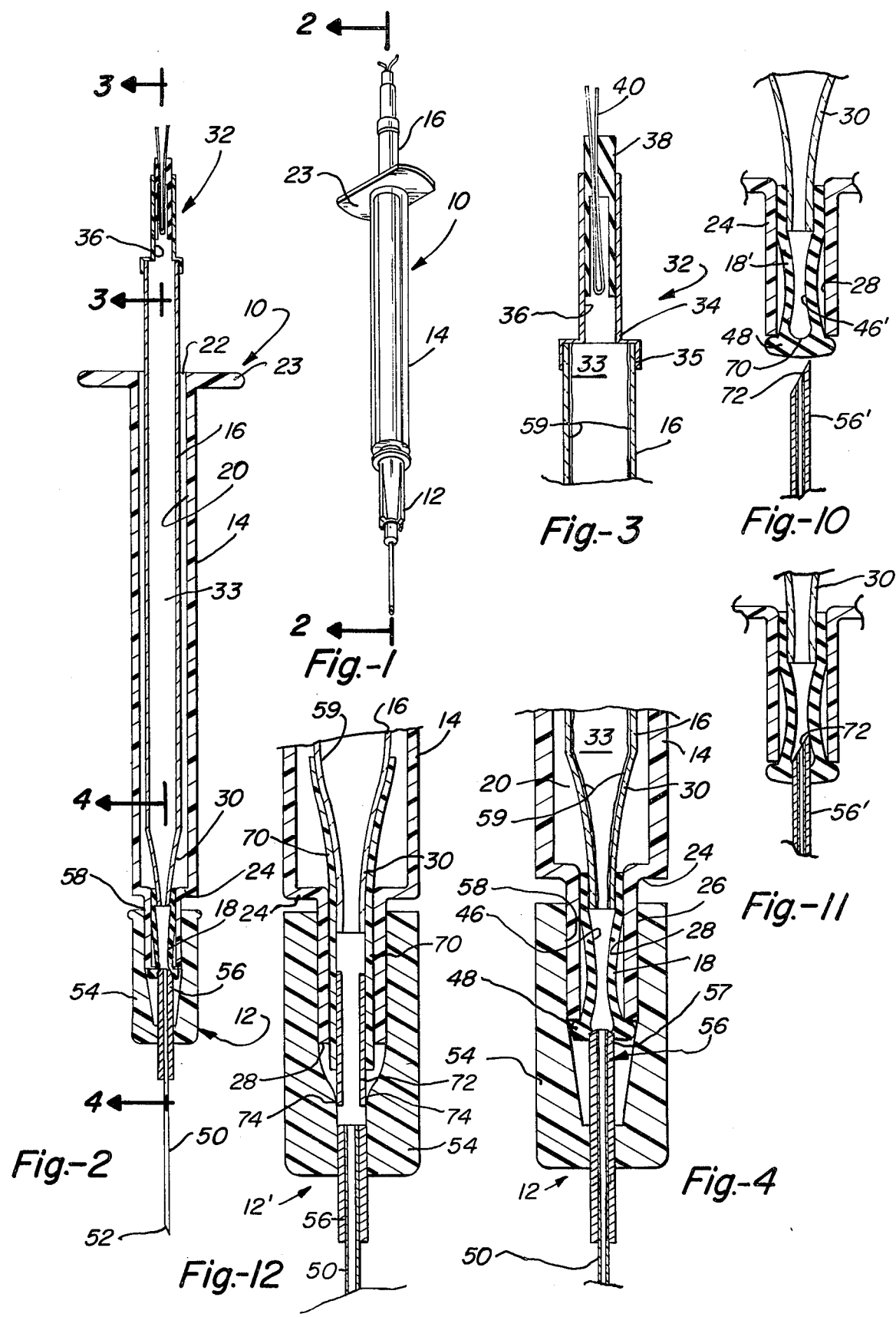

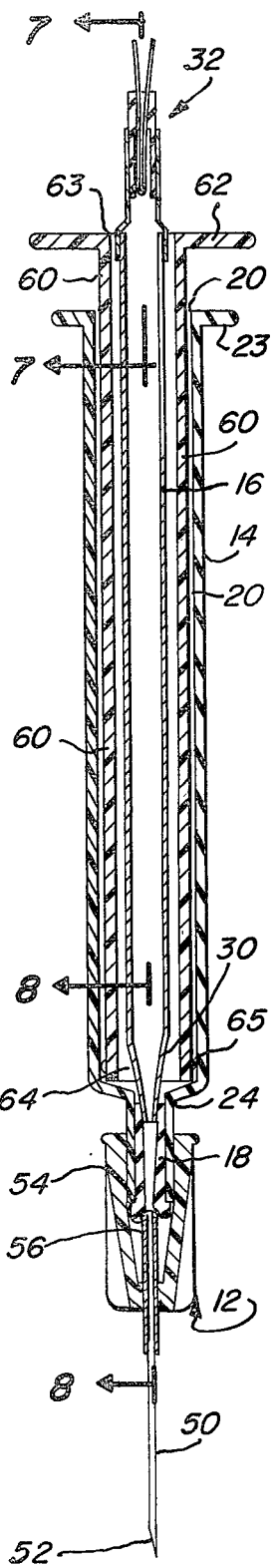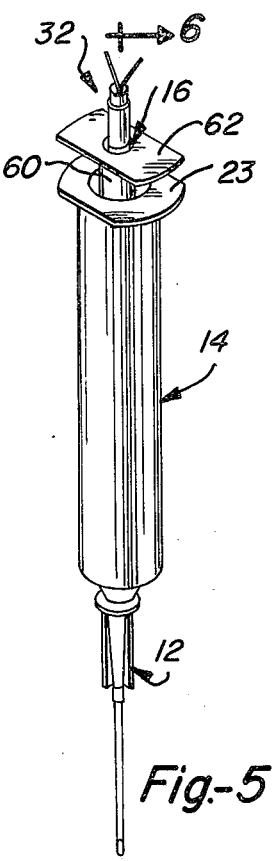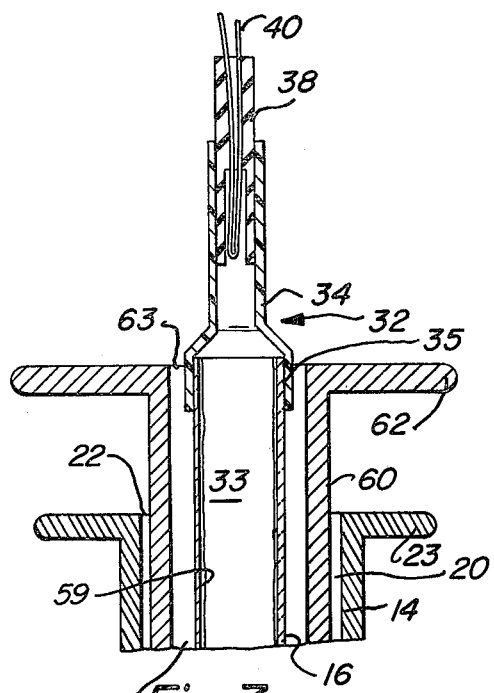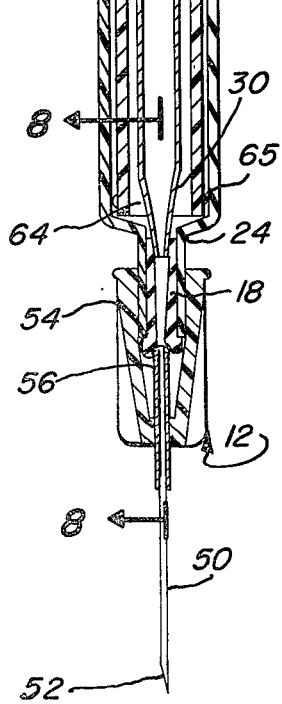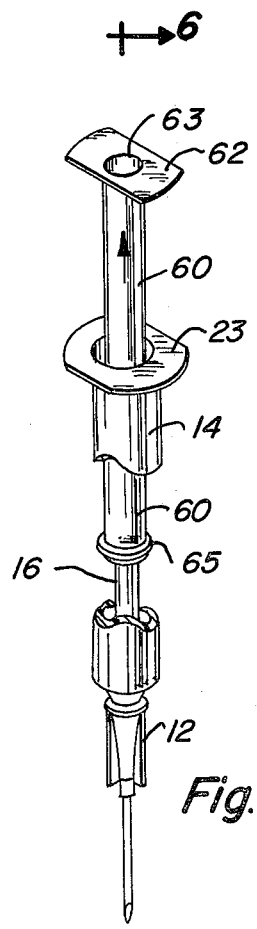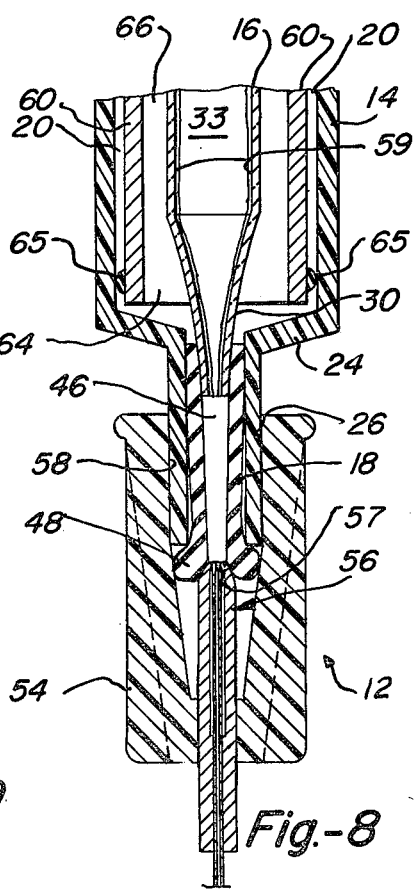

SYRINGE-LIKE APPARATUS WITH REMOVABLE CAPILLARY CARTRIDGE

BACKGROUND OF THE INVENTION

This invention relates to an apparatus for collecting a blood sample, and more particularly to a syringe-like apparatus having a hollow interior capillary cartridge for receiving a blood sample in a manner to effectively contain the collected blood sample for subsequent analysis, for example pH and blood gas analysis. More specifically the invention pertains to a capillary cartridge having fluid inlet and fluid outlet means for receiving the blood sample, for expelling air or other gaseous fluid contaminants from its interior and for effectively containing the blood sample essentially free of contamination from gases and other materials.

In blood gas analysis, it is important that contaminants not be allowed to contact or mingle with the arterially collected blood sample. Typical contaminants which could introduce significant error in analysis include air, other gases or fluids, and possibly even solid materials. It is also important that the arterially collected blood sample be prevented from clotting. To this end it is typical to precondition the container into which the blood sample is received with an anticoagulant such as heparin solution. However, with such anticoagulant solutions, the dilutent of the solution may dilute the gases in the sample or cause contamination of the sample.

Therefore, it is desirable in taking arterial blood samples for analysis to isolate the blood sample from extraneous gaseous materials and from the dilutent of the anticoagulant solution while leaving the anticoagulant itself to prevent coagulation of the blood prior to analysis.

Accordingly, it is the general object of the invention to provide a new and improved apparatus to collect at least one arterial blood sample and to effectively isolate the blood sample in a capillary cartridge or tube after collection while preventing and avoiding contamination of the collected blood sample from gases and other foreign material.

Other objects of the invention are to provide a new and improved apparatus to collect at least one arterial blood sample in which the apparatus allows use of the blood sample during an analysis, significantly reduces the probability for error in the analysis results by eliminating or reducing the probability that contaminants may enter the blood sample, effectively avoids or prevents leakage of the blood sample after collection, and is easily and conveniently constructed and used.

SUMMARY OF THE INVENTION

The present invention generally comprises a syringe-like housing member having an elongated center chamber terminated at one end by a barrel portion with means for connecting a hypodermic needle thereto, a hollow capillary cartridge or tube received within the center chamber and having fluid inlet and fluid outlet means, and sealing means for connecting the fluid inlet means of the capillary cartridge to the barrel portion of the housing member for fluid communication from an attached hypodermic needle into the interior of the capillary cartridge. The fluid outlet means of the capillary cartridge includes a fluid conductive fibrous material received within a resilient element which expands to receive the fibrous material and automatically seals upon removal of the fibrous material. The arterial blood sample passes through the fluid inlet means. Gas or air originally within the capillary cartridge is expelled through the fluid conductive fibrous material at the fluid outlet means to allow the blood sample to fill the interior of the capillary cartridge. When the capillary cartridge is filled with the blood sample, a small amount of the fluid blood is conducted by the fluid conductive fibrous material to the exterior of the resilient element thereby signalling that the capillary cartridge is full of the collected blood. The fibrous material is removed from resilient element and the resilient element seals the fluid outlet means of the capillary tube. After the hypodermic needle is removed from the artery, a stopper is placed over the flesh-piercing end of the hypodermic needle or the needle is removed to seal the blood sample within the capillary cartridge. Crystalline anticoagulant within the capillary tube prevents the sample from clotting. In another embodiment of the invention, means operatively connected for creating a pressure less than ambient pressure at the fluid outlet means of the capillary cartridge is provided for use in situations where the arterial pressure of the blood is insufficient to naturally fill the interior of the capillary cartridge.

A more complete understanding of the invention, as well as other objects and advantages, can be obtained from the following brief description of the drawings, description of a preferred embodiment and appended claims.

BRIEF DESCRIPTION OF THE DRAWINGS

FIG. 1 is a perspective view of one embodiment of the present invention in use with an attached hypodermic needle.

FIG. 2 is an enlarged section view taken along line 2—2 of FIG. 1.

FIG. 3 is an enlarged fragmentary section view taken along line 3—3 of FIG. 2 also illustrating a layer of anticoagulant deposited in the interior of one of the elements of the invention.

FIG. 4 is an enlarged section view taken along line 4—4 of FIG. 2.

FIG. 5 is a perspective view of another embodiment of the present invention in use with an attached hypodermic needle.

FIG. 6 is an enlarged section view taken along line 6—6 of FIG. 5.

FIG. 7 is an enlarged section view taken along line 7—7 of FIG. 6.

FIG. 8 is an enlarged section view taken along line 8—8 of FIG. 6 which illustrates a layer of anticoagulant deposited in the interior of one of the elements of the present invention.

FIG. 9 is a perspective view of FIG. 6 with certain portions broken out for clarity illustrating the operation of the present invention.

FIG. 10 is an enlarged fragmentary section view of an alternative embodiment of certain elements of the hypodermic needle and the invention.

FIG. 11 is an enlarged fragmentary section view of the elements of FIG. 10 illustrating cooperation of these elements in one condition of use of the present invention.

FIG. 12 is an enlarged fragmentary section view of an alternative embodiment for operatively connecting certain elements of the hypodermic needle and the invention.

DESCRIPTION OF THE PREFERRED EMBODIMENTS

Apparatus 10 for use with a hypodermic needle 12 to collect an arterial blood sample is shown in the drawings to comprise a syringe-like housing member 14, a hollow capillary cartridge or tube 16, and a resilient element or sealing means 18 which is employed, in part, to locate and position the capillary tube 16 within the housing member.

The housing member 14 shown in FIGS. 1, 2 and 4 may be an elongated tubular construction such as that of a conventional syringe-like device. The housing member 14 comprises an elongated center chamber 20 having a cylindrical configuration and a circular cross section. The chamber 20 extends axially from an open end 22 of the housing member, and typical wing portions 23 extend from the open end 22 to facilitate handling and using the syringe-like housing member 14. The opposite end of chamber 20 is terminated with a barrel portion end member 24. An axially extending and cylindrically shaped outside surface 26 serves as one form of means for connecting the hypodermic needle 12 to the barrel portion end member 24. A bore 28 extends axially through the barrel portion end member 24 and serves as one form of means adapted for providing fluid communication between the center chamber 20 and the connected hypodermic needle 12.

The capillary tube or cartridge 16 shown in FIGS. 2, 3, and 4 is received within chamber 20 of the housing member 14. The capillary tube 16 includes a fluid inlet nozzle 30, of radially inward and axially tapered configuration. The extreme end of nozzle 30 is of smaller configuration than the bore 28 in the barrel portion end member 24 and can thus be received within the bore 28. The nozzle 30 serves as one form of means for inletting fluid or a blood sample into a hollow interior or blood sample repository 33 of the capillary tube 16. A fluid outlet means 32 is connected at the other end of the capillary tube 16 opposite the nozzle 30. The fluid outlet means 32 comprises a cap member 34 sealed to the end of the capillary tube. The cap member 34 has an opening 36 axially extending therethrough for receiving a resilient member 38. The resilient member 38 expands to receive at least one length or piece of fluid conductive fibrous material such as string or thread 40 which projects through the resilient member 38 to allow fluid communication from the repository 33 of the capillary tube through the thread 40. Cap 34 is constructed of plastic material and sealed on capillary tube 16 at 35 by heat shrinking it to the end of the capillary tube at 35. The resilient member 38 may be constructed of silicone, rubber or other similar material and serves as one form of means for expanding to receive a portion of the thread 40 or other fibrous material extending through the resilient member 38 and as means for sealing the fluid outlet means 32 of the capillary tube upon removal of the fibrous material. The resilient characteristics of the member 38 close the opening through which the thread 40 was inserted upon removal of the thread. As repository 33 fills with blood, air escapes through the fluid conductive fibrous material or thread 40. Once the blood sample completely fills the repository 33, a small amount of blood is conducted through the thread 40 to signal the user that the repository 33 of the capillary tube 16 is completely filled with the blood sample. Thus constructed, the fluid outlet means 32 serves to release or outlet fluid from the interior or repository 33 of the capillary tube.

The sealing means or resilient sleeve member 18 shown in FIGS. 2 and 4 connects the fluid inlet nozzle 30 of the capillary tube 16 into the bore 28 of the barrel portion end member 24, and establishes an air-tight and fluid conductive path through the connected hypodermic needle and into the capillary tube 16. The sleeve member 18 is received within the bore 28 and comprises an opening 46 extending through the sleeve member coaxially with the bore 28. The sleeve member 18 also comprises a flange portion 48 adjacent the outer axial end of barrel portion end member 24. The nozzle end 30 of the capillary tube 16 is partially inserted into one end of the opening 46 and compresses the resilient material of the sleeve member 18 against the interior wall of the bore 28, thus causing a fluid tight seal between the fluid inlet nozzle 30 and end portion of the opening 46 of the sleeve member. The compressive forces of the resilient material of the sleeve member firmly holds the fluid inlet nozzle 30 of the capillary tube thus causing the sleeve member 18 to also serve as one form of means for positioning the capillary tube generally in an axially extending manner within the chamber 20 of the housing member 14 with the fluid inlet means or nozzle 30 oriented toward the bore 28.

The hypodermic needle 12 shown in FIGS. 2 and 4 is of a construction having an axially extending elongated hollow shaft 50 terminated with a flesh piercing point 52. The hollow shaft 50 is received within a hub member 54, and a center tubular projection member 56 is sealed to and extends from the shaft 50 within the hub member 54. An axially extending opening 58 of the hub 54 receives the barrel portion 26 of the end member 24 to attach the hypodermic needle 12 to the syringe-like housing member 14 with the surface of barrel portion 26 serving as means for frictionally connecting the hypodermic needle 12 to the housing member 14. A reduced diameter end portion 57 of the tubular projection 56 extends into and mates with the opening 46 in the sleeve member 18 adjacent the flange 48. Compression of the resilient material of the sleeve member 18 against the bore 28 of the barrel portion end member 24 establishes a fluid tight seal and a fluid conductive path between the tubular projection 56 into the sleeve member 18. Consequently, once the hypodermic needle 12 is inserted on the apparatus 10, there is a fluid tight and conductive channel from the flesh piercing point 52 of the hypodermic needle 12 into and through the capillary tube 16.

Crystalline heparin 59 or other suitable anticoagulant is deposited on the interior of the capillary tube 16 prior to use. The crystalline heparin 59 may be deposited by placing a drop of a solution of heparin into the interior of the capillary tube, and then allowing the dilutent to evaporate, thereby leaving only the solid heparin deposited on the walls of the repository 33. This process can be expedited by heating the capillary tube to hasten the evaporation. The crystalline heparin 59 or other suitable anticoagulant prevents the blood sample from coagulating in the capillary tube after it has been collected.

In use of the apparatus 10, the capillary tube 16 is received within the housing member 14 with the nozzle 30 being sealed within the bore 28 of the end member barrel portion 24 by the sleeve member 18. The user attaches the hypodermic needle 12 causing the end portion 57 of the tubular projection 56 to be received within the opening 46 through the sleeve member 18. The flesh piercing point is inserted in an artery of a person from whom the blood sample is collected. The blood pressure within the artery forces blood upward through the hollow shaft 50 and tubular projection 56, through the opening 46 in the sleeve member 18 and into the fluid inlet nozzle 30 the capillary tube 16. The hollow interior or repository 33 gradually fills because of the blood pressure in the artery and because the fibrous material or thread 40 of the fluid outlet means 32 expels air to allow the repository 33 to fill with blood. After all air in the interior of the capillary cartridge has been conducted from the capillary tube through thread 40, a small amount of the blood sample is conducted by the thread 40 through the resilient member 38 forming a drop on the top of the resilient member 38. The drop of blood signals the operator to remove the hypodermic needle from the artery thereby terminating the blood sample collection. A cork or stopper is immediately placed over the flesh piercing point 52 of the hypodermic needle to seal the hollow opening through the needle shaft 50. The portion of the thread 40 extending exteriorally of the resilient member 28 is grasped and the thread is pulled from the resilient member. The resilient member contracts thereby sealing the hole which once received the thread 40 and seals the fluid outlet means of the capillary cartridge. In this manner the collected blood sample is maintained in a protected and sealed environment within the capillary cartridge essentially free of influence by air, gases or other potential contaminants until such time as the collected blood sample is analyzed. The crystalline heparin 59 which dissolves when the blood sample enters the respository 33 of capillary tube 16, prevents the blood sample from coagulating while in the repository.

Another embodiment of the present invention is intended for use where the arterial blood pressure is insufficient to naturally fill the interior of the capillary tube 16 with a blood sample. In addition to the elements shown and described in conjunction with FIGS. 1 to 4, the other embodiment of the invention, shown in FIGS. 5 to 9, also comprises means operatively connected for selectively creating a pressure less than ambient pressure at the fluid outlet means 32 of the capillary tube 16. A slide member 60 may take the form of one such means.

The slide member 60 shown in FIGS. 5 to 9 is of hollow elongated cylindrical construction having a circular cross section and opposite open ends 63 and 64. The slide member 60 is received in the chamber 20 of the housing member 14 coaxially intermediate the capillary tube 16 and the housing member. Wing portions 62 extend laterally from slide member 60 at the open end 63 adjacent the fluid outlet means 32 of the capillary tube, and serve as means for gripping the slide member. Attached to the slide member 60 adjoining the other open end 64 is an O-ring member 65 extending concentrically between the slide member 60 and the walls of the chamber 20 of the housing member 14. The O-ring member 65 serves as one form of gasket means for creating a gas restrictive seal intermediate the slide member and the chamber of the housing during use.

To use a slide member to create a pressure less than ambient pressure at the fluid outlet means 32 of the capillary tube 16, the wing portions 62 are grasped by the operator and the slide member 60 is moved axially as shown in FIG. 9 until the fluid outlet means 32 is within the hollow interior 66 (FIG. 7) of the slide member 60. At this point the operator places the thumb, for example, over the exposed open end 63. The thumb creates a seal over the open end 63 of the slide member and as the slide member is further moved axially as shown in FIG. 9 a pressure less than ambient pressure is created in the hollow interior. The lower pressure in the interior 66 of the slide member 60 is prevalent at the fluid outlet means 32 thereby creating a pressure less than ambient pressure within the repository 33 of the capillary tube 16 as a result of the fluid conductive properties of the thread 40. In this manner the operator may assist the collection of the blood sample in the capillary tube by reducing the pressure in the capillary tube against which the arterial pressure of the blood must work to fill the respository of the capillary tube. After collection of the sample, the thumb may be removed from the end 63 and the slide member 60 may be removed from the housing member or moved back to its original position in the housing member to gain access to the thread 40 in the resilient member 38 at the fluid outlet means 32. The thread 40 is removed and the flesh piercing point 52 of the hypodermic needle is capped in the same manner as has been described previously to protect and seal the collected blood sample from contamination.

Alternative embodiments of a sleeve member 18' and a center tubular projection member 56' of the hypodermic needle 12, which may be employed in substitution for the previously described corresponding elements 18 and 56, are shown in FIGS. 10 and 11. The sleeve member 18' comprises an opening 46' extending partially through the sleeve member 18' coaxially with the bore 28 of the barrel portion end member 24. A membrane 70 formed of the same resilient material as the sleeve member 18', closes and seals the opening 46' at its outer end. The projection member 56' of the hypodermic needle is provided with a sharpened end 72 for the purpose of piercing the membrane 70, as is shown in FIG. 11, when the hypodermic needle 12 is attached to the apparatus 10.

Once the sharpened end 72 of the projection member 56' has pierced the membrane 70 of the sleeve member 18', a fluid tight seal and fluid conductive path is established from the hollow interior of the tubular projection member into the opening 46'. Upon removal of the projection member 56 from the sleeve member 18' the resilient material of the membrane 70 seals the opening formed in the membrane to contain the blood sample within the capillary tube 16 and opening 46'.

After collection of the blood sample the capillary tube 16 can be removed from the chamber 20 out of the open end 22 of the housing member 14. The flange 48 deflects inwardly to allow the sleeve member 18' to slide through the bore 28 in the barrel portion end member 24 without becoming disconnected from the fluid inlet nozzle 30 of the capillary tube. Thus, with use of sleeve member 18' the capillary tube may be removed with the blood sample sealed therein by the sleeve member 18' and the resilient member 38 of the fluid outlet means 32.

Another arrangement for operatively connecting a hypodermic needle 12' with the nozzle 30 of the capillary tube 16 is illustrated in FIG. 12. A length of heat shrink tubing 70 is inserted over the nozzle 30 and over a tubular tip member 72 aligned with the nozzle, and the heat shrink tubing is heated to contract around the nozzle and tubular tip member 72. The tip member is thus sealed to the nozzle 30 and a fluid tight path is established from the interior of the capillary tube 16 through the tip member 72. The nozzle 30, the heat shrink tubing 70, and tubular tip member 72 are positioned within the bore 28 of barrel portion end member 24.

The hypodermic needle 12' employs the hub member 54 attached to the projection member 56 which receives the needle shaft 50. A conically shaped receptacle 74 is formed in the hub member 54 adjacent the end of the projection member 56 as is typical in some hypodermic needles. With the needle 12' attached to the barrel portion end member 24, a fluid tight friction fit is established by insertion of the tubular tip member 72 into the receptacle 74, thus establishing a fluid conductive path through the needle shaft into the capillary tube 16.

After collection of the blood sample, the capillary tube 16 and the attached tubular tip member 72 can be removed from the housing member 14, and clay is placed in the hollow outer end of the tubular tip member 72 to seal the tip member.

It is within the scope of the present invention to include more than one capillary tube within the chamber 20 of the housing member 14. The plurality of the capillary tubes may be connected in series so that each fills sequentially with the collected blood, thereby providing a number of separate repositories for collected arterial blood samples. Suitable fluid conductive means may also be employed whereby multiple capillary tubes may be connected in parallel with the opening 48 through the sealing means, if desired.

Embodiments of the present invention have been shown and described with a degree of particularity to enable a complete and full understanding of those embodiments. It should be understood that the present invention involves the inventive concepts defined in the appended claims, and these inventive concepts are not intended to be limited except insofar as the prior art requires.

What is claimed is:

1. Apparatus for use with a hypodermic needle to collect at least one blood sample, comprising:
   a housing member comprising an elongated center chamber and an end member terminating the center chamber, the end member having means for connecting a hypodermic needle thereto, and the end member further having bore means extending through the end member adapted for fluid communication between the center chamber and a connected hypodermic needle;
   a hollow capillary tube positioned within the center chamber of said housing member in a stationary manner, said capillary tube comprising fluid inlet means and fluid outlet means connected for fluid communication therebetween, and
   sealing means for releasably retaining and connecting the fluid inlet means of said capillary tube to the bore means of the end member of said housing member in a fluid tight relationship for fluid communication through the bore means into the fluid inlet means.

2. Apparatus as recited in claim 1 wherein the fluid outlet means of said capillary tube comprises:
   fluid conductive fibrous material;
   resilient means for expanding to receive a portion of said fibrous material extending through said resilient means and for sealing the fluid outlet means upon removal of said fibrous material from said resilient means.

3. Apparatus as recited in claim 2 further comprising:
   cap means for supporting the resilient means at the fluid outlet means of said capillary tube.

4. Apparatus as recited in claim 1, wherein:
   the fluid inlet means of said capillary tube comprises an inlet nozzle;
   the inlet nozzle is received within the bore means of the end member of said housing, and
   said sealing means comprises sleeve means between the bore means and the nozzle for sealing the nozzle into the bore means.

5. Apparatus as recited in claim 4 wherein the sleeve means comprises resilient material.

6. Apparatus as recited in claim 1 further comprising:
   means operative for selectively creating a pressure less than ambient pressure at the fluid outlet means of said capillary tube.

7. Apparatus as recited in claim 6 wherein said means for creating a pressure less than ambient pressure comprises:
   a hollow cylindrical slide member received within the center chamber of said housing intermediate the capillary tube and the housing member.

8. Apparatus as recited in claim 7 further comprising:
   gasket means for creating a gas restrictive seal intermediate said slide member and the interior wall of said housing.

9. Apparatus as recited in claim 8 wherein said gasket means allows longitudinal movement of said slide member within said center chamber.

10. Apparatus for use with a hypodermic needle to collect an arterial blood sample, comprising:
    an elongated tubular housing member having an axially-extending chamber and an end member having a bore therethrough, the end member further having means in conjunction with the bore for connecting a hypodermic needle for fluid communication with the chamber;
    a hollow elongated capillary tube having a fluid inlet nozzle, a blood sample repository and a fluid outlet means;
    means for positioning said capillary tube generally in an axially extending manner within the chamber of said housing member with the fluid inlet nozzle oriented toward the bore; and
    sleeve means within the end member of the housing member for connecting the fluid inlet nozzle of said capillary tube in a fluid conductive relationship through the bore of the end member.

11. Apparatus as recited in claim 10 wherein said sleeve means comprises:
    a sleeve member comprised of resilient material having an opening therethrough, said sleeve member being received in the bore with the opening extending through the bore.

12. Apparatus as recited in claim 10 wherein:
    the end member of said housing member comprises an axially extending barrel portion having a generally cylindrically shaped outer configuration and the bore being formed axially therethrough, the outside surface of said barrel portion comprising means for connecting a hypodermic needle, and
    said sleeve means comprises a sleeve member of resilient material received in the bore of the barrel portion, the sleeve member having an opening extending coaxially through the bore and a flange portion extending generally transversely at the end of the barrel portion.

13. Apparatus as recited in claim 12 wherein:
a portion of the fluid inlet nozzle of said capillary tube is received within the bore of the barrel portion, and
a portion of the fluid inlet nozzle of said capillary tube is received within the opening in the sleeve member in a fluid tight relationship.

14. Apparatus as recited in claim 13 wherein the fluid outlet means comprises:
a cap member sealed in a fluid tight relationship to the end of said capillary tube opposite said fluid inlet nozzle,
a length of fluid conductive fibrous material, and
resilient means for expanding to receive a portion of said fibrous material to communicate fluid from the interior to the exterior of said capillary tube and for sealing upon removal of the fibrous material, said resilient means retained within the cap member.

15. Apparatus as recited in claim 14 wherein the chamber of said housing member is generally cylindrically shaped, and said apparatus further comprising:
a hollow elongated slide member received within the chamber of said housing member generally intermediate the capillary tube and the chamber.

16. Apparatus as recited in claim 15 further comprising:
gasket means intermediate said slide member and the interior wall of the housing for creating a fluid seal between the slide member and the housing.

17. Apparatus as recited in claim 10 further comprising:
means operatively connected for selectively creating a pressure less than ambient pressure at the fluid outlet means of said capillary tube.

18. Apparatus for use with a hypodermic needle to collect an arterial blood sample, comprising:
an elongated tubular housing member having one open end and an opposite end terminated by a barrel portion, the barrel portion comprising means for connecting a hypodermic needle and bore means extending coaxially through the barrel portion for fluid communication between a connected hypodermic needle and the interior of said tubular housing member;
a hollow elongated capillary tube having a fluid inlet nozzle and a fluid outlet means, said capillary tube received within the interior of said tubular housing member with the fluid inlet nozzle oriented within the bore means of said housing member;
a resilient sleeve member within the bore means;
an opening extending through the sleeve member coaxially with the bore means; and
the fluid inlet nozzle of said capillary tube being received within the opening of the sleeve member in a fluid tight relationship.

19. Apparatus as recited in claim 18 wherein the sleeve member further comprises a flange portion adjacent an axial end of said barrel portion.

20. Apparatus as recited in claim 19 wherein the flange portion of said sleeve member is adjacent the end of the barrel portion axially opposite the interior of said tubular housing member.

21. Apparatus as recited in claim 18 wherein the fluid outlet means of said capillary tube comprises:
a cap member having an axially extending opening therethrough, said cap member being sealed to the end of said capillary tube opposite the fluid inlet nozzle;
at least one length of fluid conductive fibrous material,
resilient means received within the opening of said cap member for expanding to receive a portion of each length of fibrous material extending essentially axially through said resilient means and for sealing the opening in said cap member upon removal of the fibrous material.

22. Apparatus as recited in claim 18 further comprising:
a cylindrically shaped elongated slide member having opposite open ends coaxially received within the tubular housing member radially exterior of said capillary tube, and
means operatively connected for creating a fluid seal between the slide member and the interior of said tubular housing member.

23. Apparatus as recited in claim 22 wherein said tubular housing member comprises laterally extending wing portions.

24. Apparatus for use with a conventional syringe-like housing member and a hypodermic needle to collect at least one arterial blood sample, said syringe-like housing member being of conventional construction comprising an elongated cylindrically shaped tubular housing member having one open end and an opposite end member barrel portion having a bore therethrough to operatively establish a fluid communication passage from the interior of the tubular housing member, said inventive apparatus comprising:
at least one hollow elongated capillary cartridge having a fluid inlet means and a fluid outlet means connected for fluid communication therebetween, and
means received within the bore of the end member barrel portion of the housing member for releasably retaining and supporting the capillary cartridge in an axially extending stationary position within the interior of the housing member with the fluid inlet means oriented toward the bore and for connecting the fluid inlet means of the capillary tube in a fluid conductive relationship through the bore to the hollow interior of the hypodermic needle.

25. Apparatus as recited in claim 24 wherein said supporting and connecting means comprises:
a resilient sleeve member adapted to be inserted coaxially within the bore of the end member barrel portion of the syringe housing member, said sleeve member having an opening extending at least partially therethrough for receiving the fluid inlet means of said capillary tube within the bore.

26. Apparatus as recited in claim 25 wherein said resilient sleeve member further comprises
a flange portion protruding from the end portion of the bore of the end member barrel portion.

27. Apparatus as recited in claim 24 wherein the fluid outlet means of said capillary tube comprises:
fluid conductive fibrous material.

28. Apparatus as recited in claim 27 wherein the fluid outlet means of said capillary means further comprises:
resilient means for expanding to receive a portion of said fibrous material extending through said resilient means and for sealing upon removal of said fibrous material from said resilient means.

29. Apparatus as recited in claim 28 further comprising:

a cap member sealed to the capillary tube and having an opening therethrough for receiving said resilient means.

30. Apparatus as recited in claim 26 wherein said hypodermic needle comprises:
   hub member having means for receiving and mating with the connection means of said syringe-like housing member;
   a hollow shaft extending from the hub member; and
   a hollow tubular projection member operatively attached to the hub member and hollow shaft to project into and seal with the opening in the sleeve member.

31. Apparatus as recited in claim 30 wherein said resilient sleeve member comprises:
   membrane means for sealing and closing the opening through said sleeve member and for expanding to receive the tubular projection member of said hypodermic needle.

32. Apparatus as recited in claim 18 further comprising:
   resilient membrane means within the opening extending through the sleeve member for yieldably closing and sealing the opening.

33. Apparatus as recited in claim 10 wherein said sleeve means comprises heat shrink tubing.

34. Apparatus as recited in claim 18 wherein said sleeve member comprises heat shrink tubing sealed to the inlet nozzle of said capillary tube.

35. Apparatus as recited in claim 34 further comprising:
   a tubular tip member operatively sealed to the inlet nozzle of said capillary tube by said heat shrink tubing.

36. Apparatus as recited in claim 25 further comprising:
   a tubular tip member, and wherein:
   said resilient sleeve member comprises a length of heat shrink tubing operatively connecting the fluid inlet means of said capillary cartridge and said tubular tip member.

37. Apparatus as recited in claim 36 wherein:
   said hypodermic needle further comprises a hub member attached with the hollow shaft at the end opposite the flesh-piercing end, and a receptacle adjacent an end of the hollow shaft; and
   tubular tip member is adapted to be frictionally received in the receptacle of said hypodermic needle.

38. Apparatus for use with a hypodermic needle to collect at least one blood sample, comprising:
   a housing member comprising an elongated center chamber and an end member terminating the center chamber, the end member having means for connecting a hypodermic needle thereto, and the end member further having bore means extending through the end member adapted for fluid communication between the center chamber and a connected hypodermic needle;
   a hollow capillary tube positioned within the center chamber of said housing member, said capillary tube comprising fluid inlet means and a fluid outlet means connected for fluid communication therebetween, said fluid outlet means including fluid conductive fibrous material and resilient means for expanding to receive a portion of said fibrous material extending through said resilient means and for sealing the fluid outlet means upon removal of said fibrous material from said resilient means, and
   sealing means for connecting the fluid inlet means of said capillary tube to the bore means of the end member of said housing member in a fluid tight relationship for fluid communication through the bore means into the fluid inlet means.

39. Apparatus for use with a conventional syringe-like housing member and a hypodermic needle to collect at least one arterial blood sample, said syringe-like housing member being of conventional construction comprising an elongated cylindrically shaped tubular housing member having one open end and an opposite end member barrel portion having a bore therethrough to operatively establish a fluid communication passage from the interior of the tubular housing member, said inventive apparatus comprising:
   at least one hollow elongated capillary cartridge having a fluid inlet means and a fluid outlet means connected for fluid communication therebetween, and
   a resilient sleeve member adapted to be inserted coaxially within the syringe housing member, said sleeve member having an opening extending at least partially therethrough for receiving the fluid inlet means of said capillary tube within the bore of said sleeve member adapted to support the capillary cartridge in an axially extending position within the interior of the housing member with the fluid inlet means oriented toward the bore and for connecting the fluid inlet means of the capillary tube to the hollow interior of the hypodermic needle.

* * * * *